United States Patent
Graeve

(10) Patent No.: US 10,369,284 B2
(45) Date of Patent: Aug. 6, 2019

(54) KIT, USE THEREOF AND METHOD FOR FILLING CONNECTIVE TISSUE OF THE SKIN

(71) Applicant: Amedrix GmbH, Esslingen (DE)

(72) Inventor: Thomas Graeve, Stuttgart (DE)

(73) Assignee: MEIDRIX BIOMEDICALS GMBH, Esslingen (DE)

( * ) Notice: Subject to any disclaimer, the term of this patent is extended or adjusted under 35 U.S.C. 154(b) by 0 days.

(21) Appl. No.: 14/417,402

(22) PCT Filed: Jul. 15, 2013

(86) PCT No.: PCT/EP2013/064917
§ 371 (c)(1),
(2) Date: Jan. 26, 2015

(87) PCT Pub. No.: WO2014/019842
PCT Pub. Date: Feb. 6, 2014

(65) Prior Publication Data
US 2015/0202364 A1    Jul. 23, 2015

(30) Foreign Application Priority Data
Jul. 31, 2012   (DE) .................. 10 2012 213 496

(51) Int. Cl.
| | |
|---|---|
| *A61K 9/00* | (2006.01) |
| *A61M 5/19* | (2006.01) |
| *A61K 38/39* | (2006.01) |
| *A61L 27/24* | (2006.01) |
| *A61L 27/60* | (2006.01) |

(52) U.S. Cl.
CPC .............. *A61M 5/19* (2013.01); *A61K 9/0021* (2013.01); *A61K 9/0024* (2013.01); *A61K 38/39* (2013.01); *A61L 27/24* (2013.01); *A61L 27/60* (2013.01)

(58) Field of Classification Search
CPC ......... A61L 27/24; A61L 27/60; A61K 38/39; A61K 9/0021; A61K 9/0024; A61M 5/19
See application file for complete search history.

(56) References Cited

U.S. PATENT DOCUMENTS

| | | | |
|---|---|---|---|
| 5,366,498 A | 11/1994 | Brannan et al. | |
| 5,428,024 A | 6/1995 | Chu et al. | |
| 2004/0030404 A1 | 2/2004 | Noll et al. | |
| 2008/0103564 A1 | 5/2008 | Burkinshaw et al. | |
| 2009/0254104 A1 | 10/2009 | Murray | |
| 2013/0324473 A1 | 12/2013 | Graeve | |

FOREIGN PATENT DOCUMENTS

| | | |
|---|---|---|
| DE | 10026789 A1 | 12/2001 |
| DE | 102007044983 A1 | 4/2009 |
| EP | 0632820 A1 | 1/1995 |
| EP | 1221937 B1 | 12/2004 |
| WO | WO-93/017075 A1 | 9/1993 |
| WO | WO-2012/107174 A1 | 8/2012 |

OTHER PUBLICATIONS

Syringe Needle Gauge Chart, from http://www.sigmaaldrich.com/chemistry/stockroom-reagents/learning-center/technical-libr . . . , pp. 1-2, accessed Oct. 9, 2014.*
Zhang et al, Preparation and Characterisation of Collagen from Freshwater Fish Scales, Food and Nutrition Sciences, 2011, 2, pp. 818-823.*
Varghese et al, Hydrogels for Musculoskeletal Tissue Engineering, Adv Polym Sci, 2006, 203, pp. 95-144.*
Sung et al, Control of 3-dimensional collagen matrix polymerization for reproducible human mammary fibroblast cell culture in microfluidic devices, Biomaterials, 2009, 30, pp. 4833-4841.*
Kablik et al, Comparative Physical Properties of Hyaluronic Acid Dermal Fillers, Dermatol Surg, 2009, 35, pp. 302-312.*
Needle Selection Continuum, from Vitality Medical, p. 1, 2013.*
Syringes and Needles, from http://pharmlabs.unc.edu/labs/parenterals/syringes.htm, pp. 1-2, accessed Apr. 27, 2017.*
Administration of Parenteral Medications, Sep. 4, 2008, pp. 835-882.*
English Translation of International Preliminary Report on Patentability and Written Opinion regarding International Application No. PCT/EP2013/064917, dated Sep. 25, 2013.
International Search Report (English and German) and Written Opinion of the ISA (German) for PCT/EP2013/064917, ISA/EP, Rijswijk, NL, dated Sep. 25, 2013.
Kablik et al, "Comparative Physical Properties of Hyaluronic Acid Dermal Fillers", Dermatol Surg, 35, pp. 302-312 (2009).
Office Action regarding German Application No. 10 2012 213 496.4, dated Jan. 2, 2017. Machine translation provided.

* cited by examiner

*Primary Examiner* — Karlheinz R. Skowronek
*Assistant Examiner* — Li N Komatsu
(74) *Attorney, Agent, or Firm* — Stephen T. Olson; Harness, Dickey & Pierce, P.L.C.

(57) ABSTRACT

The invention concerns a kit and a syringe for use in a therapeutic method for intracutaneous filling of the collagen structure in connective tissue of the skin, and the use thereof, particularly as part of the treatment of skin defects, particularly skin diseases and signs of skin aging.

18 Claims, 6 Drawing Sheets

KIT, USE THEREOF AND METHOD FOR FILLING CONNECTIVE TISSUE OF THE SKIN

CROSS-REFERENCE TO RELATED APPLICATIONS

This application is a 371 U.S. National Stage of International Application No. PCT/EP2013/064917, filed Jul. 15, 2013, which claims priority to German Patent Application No. 10 2012 213 496.4, filed Jul. 31, 2012. The entire disclosures of each of the above applications are incorporated herein by reference.

The invention relates to a kit and a syringe for use in a therapeutic method for intracutaneous filling of the collagen structure in connective tissue of the skin and to the use thereof, particularly as part of treating skin defects, particularly skin diseases and signs of skin aging.

A collagen-based biomatrix and a method for producing the same are known from DE 10 026 789 A1. A collagen biomatrix is produced from collagen extracted from rat tail tendons. To this end, the acidic collagen solution present after extraction is neutralized under refrigeration with a serum-containing buffer and, optionally in the presence of cells, cast into a collagen gel, which eventually gels or cross-links, in other words cures, into a collagen-containing biomatrix, which can be conserved as a prefabricated cell-free collagen implant or as a cell-containing collagen transplant with embedded chondrocytes.

US 2009/0254104 A1 discloses methods and collagen-containing products for treating tissue defects. Disclosed in particular are collagen-containing matrices, which are introduced for the reconstruction of, for example, tendons in a patient. The moldability or shapability of the introduced collagen-containing matrix for forming a desired three-dimensional structure of the implant, however, is only possible to a limited extent in situ.

EP 1 221 937 B1 discloses compositions containing insoluble collagen fibrils, cells, and microcarriers from 0.1 to 2 mm in size, which can be introduced into the tissue being treated in liquid form by means of, for instance, syringes, where they can gel into a solid matrix in situ. This coarse particle composition, however, does not permit an intracutaneous application of moldable collagen with a minimum amount of pain.

EP 0 632 820 B1 discloses highly concentrated, homogenized collagen compositions that can also be injected with high collagen concentration into tissue to be treated. These specially prepared, highly concentrated, injectable collagen compositions, however, are non-gellable and therefore not suitable for creating a moldable three-dimensional structure in a tissue to be treated.

Hence there is still a need for methods and means that will allow better treatment of skin defects (e.g., wrinkles) arising in the context of skin diseases and signs of aging and identified as undesirable by the patient, particularly in order to achieve an as-natural-as-possible reconstruction of the natural complexion, especially of the outer contour of the skin, in a manner as gentle as possible for the patient.

The invention addresses the technical problem of providing methods and means for producing a collagen-based matrix in situ, which in particular can be used to treat skin defects in the bodies of humans or animals and with which the disadvantages of the prior art can be avoided.

For solving this technical problem, the invention provides a method in which a liquid, gellable collagen composition is obtained from a liquid, particularly concentrated, collagen solution in combination with a liquid buffer solution. The latter is suitable for direct intracutaneous injection into the dermis of a patient, where it immediately cures into a collagen matrix, which then forms the skin implant directly in situ. Introducing the liquid gelling collagen composition into the dermis thus enables three-dimensional shaping, e.g., better adaptation to the outer contour of the body part in question. In particular, immediately after injection the still-liquid collagen composition can be shaped, i.e., molded, i.e., three-dimensionally modeled before it gels, i.e., cures.

The invention is advantageous in that it enables the injection of a liquid collagen composition into the tissue site to be treated (i.e., the dermis), wherein the liquid collagen composition gels locally at the site being treated, wherein the composition can still be molded immediately after injection by the surgeon, for example, in the desired manner, namely three-dimensionally into the desired shape. Surprisingly, it is possible to administer a highly viscous liquid collagen composition with a comparatively high collagen concentration intracutaneously to a patient through a syringe needle with a very small inner diameter in an essentially painless manner, without the needle becoming plugged. This is in particular all the more surprising in that the liquid collagen composition employed contains a gellable collagen. Preference is given to the liquid gellable collagen composition having a viscosity of preferably 1 to 9 Pa·s, in particular 1.2 to 8 Pa·s, preferably 2 to 9 Pa·s, in particular 3.5 to 8 Pa·s, in particular 2.7 to 7 Pa·s, in particular 2.8 to 6 Pa·s, in particular 2.9 to 5.5 Pa·s, in particular for collagen concentrations of 6 to 10 mg/mL.

In a particularly preferred embodiment, provision is made such that the liquid gellable collagen composition has a viscosity of 2 to 9 Pa·s, in particular 2.5 to 8 Pa·s, in particular 2.7 to 7 Pa·s, in particular 2.8 to 6 Pa·s, in particular 2.9 to 5.5 Pa·s, in particular 2.5 to 3 Pa·s, for a collagen concentration of 8 mg/ml.

In a particularly preferred embodiment, a viscosity of the liquid gellable collagen composition of preferably 2 to 9 Pa·s, in particular 3.5 to 8 Pa·s, in particular 2.7 to 7 Pa·s, in particular 2.8 to 6 Pa·s, in particular 2.9 to 5.5 Pa·s, in particular 5.0 to 5.5 Pa·s, for a collagen concentration of 10 mg/mL is provided.

In a particularly preferred embodiment, a viscosity of the liquid gellable collagen composition of 1 to 2 Pa·s, in particular 1.2 to 1.4 Pa·s, in particular 1.25 to 1.35 Pa·s, for a collagen concentration of 6 mg/mL collagen is provided.

The viscosity is preferably determined according to the method described in Example 3 and the devices used therein.

The invention enables the supplying of a collagen-containing biomatrix or a collagen implant in vivo in a patient's skin, preferably the dermis, with a high ratio of non-denatured, cross-linkable collagen of native structure. The present invention in particular enables the introduction of a large quantity of highly concentrated gellable collagen directly into the tissue site being treated, which advantageously leads to particularly high stability of the preferably molded three-dimensional collagen structure thus obtained, which is furthermore characterized by particularly long durability. Owing to the fact that the method of the invention allows the collagen composition thus produced to be transported to the application site, namely the dermis, while still in liquid form, less large accesses are required. The invention makes improved minimally invasive surgery possible and thus reduces the trauma induced by the surgical procedure. It has been shown that locally present skin cells proliferate especially well in a collagen biomatrix and have a high rate of autologous collagen synthesis if a high percentage of native collagen is contained in the biomatrix. The invention thus avoids collagen-denaturing measures.

In connection with the present invention, the term skin is understood to mean the superficial organ of the human or animal body serving to delimit the inside and the outside of the human or animal body, which is divided into the epidermis, the immediately underlying dermis, also known as corium or connective tissue, and the subcutis. According to the invention, provision is made for reconstituting the collagen structure of the connective tissue of the skin, in other words the collagen structure located in the dermis.

In connection with the present invention, "skin" is also understood to include the mucosa, in particular lips.

In connection with the present invention, "intracutaneous injection" is understood to mean that the needle of the syringe used for injection penetrates into the dermis, i.e., the connective tissue of the skin, and that the liquid gellable collagen composition is deposited within the skin.

In a preferred embodiment, the present invention provides a kit for use in a therapeutic method for intracutaneous filling of the collagen structure in connective tissue of a patient's skin, comprising at least one container containing a collagen solution, at least one container containing a neutralizing buffer solution, and a syringe suited for intracutaneous injection of the collagen and buffer solution, wherein the needle of the syringe has an outer diameter (also known in the following as diameter of the needle, in particular of the needle cannula) of 0.3 to 0.4 mm, in particular 0.32 to 0.38 mm, and preferably 0.35 mm.

According to the invention, the outer diameter of the needle of the syringe used according to the invention preferably has a diameter of 0.3 mm, which corresponds to 30 gauge.

In another preferred embodiment, a kit of the present invention is provided in which the syringe has at least two separate containers configured as chambers, which are in fluid connection with a mixing device arranged in the syringe and with the needle of the syringe, wherein at least a first chamber is filled with the collagen solution and at least a second chamber separated therefrom is filled with the neutralizing buffer solution, and wherein the needle, in particular the needle cannula, of the syringe has a diameter of 0.3 to 0.4 mm, preferably 0.3 mm, in particular 0.32 to 0.38 mm, and preferably 0.35 mm.

In another preferred embodiment, a kit of the present invention is provided in which the mixing device is a static mixer.

The present invention can make provision such that a) the aforementioned containers of the kit are separate from the syringe, b) the aforementioned containers are separate from the syringe and are configured as reversibly or irreversibly attachable to the syringe, or c) the aforementioned containers are an integral component of the syringe.

In a preferred embodiment of the present invention, along with the components specifically mentioned above, namely the syringe, optionally separate chambers, and buffer and collagen solution, a kit of the invention further comprises a packaging and/or written instructions for use, especially one indicating that the kit and/or its components can be used in a therapeutic method for intracutaneous filling of the collagen structure in connective tissue of the skin, in particular that of a patient with skin defects such as signs of skin aging or skin diseases.

In a preferred embodiment, the present invention provides a syringe for use in a therapeutic method for intracutaneous filling of the collagen structure in connective tissue of a patient's skin, which comprises at least two separate containers configured as chambers, which are in fluid connection with a mixing device arranged in the syringe and with the needle of the syringe, wherein at least a first chamber is filled with a collagen solution and at least one second chamber separated therefrom is filled with a neutralizing buffer solution, wherein the needle of the syringe has a diameter of 0.3 to 0.4 mm, preferably 0.3 mm, in particular 0.32 to 0.38 mm, and preferably 0.35 mm.

In a preferred embodiment, the present invention provides a method for intracutaneous filling of the collagen structure in connective tissue of a patient's skin by means of a collagen gel, comprising the steps:
   a) separate supplying of a collagen solution and of a neutralizing buffer solution,
   b) mixing of the collagen solution and the neutralizing buffer solution, wherein a gellable collagen composition is obtained,
   c) intracutaneous injection of the liquid gellable collagen composition before the gelling thereof, and
   d) shaping of the injected liquid gellable collagen composition at the intracutaneous target site, wherein the shaped collagen gel cures in the target site.

In another preferred embodiment, a method of the present invention is provided in which the collagen solution and the buffer solution are each brought separately to a temperature of 20° C. to 37° C. in method step a), and the tempered collagen solution and the tempered buffer solution are mixed in method step b), wherein a liquid gellable collagen composition is obtained.

In another preferred embodiment, a method of the present invention is provided wherein in method step b) the collagen and neutralizing buffer solutions mixed with one another (i.e., the liquid gellable collagen composition) are brought to a temperature of 20 to 37° C.

In another preferred embodiment, provision is made such that the collagen solution and the neutralizing buffer solution supplied in method step a) are at a temperature of −15 to 19° C., preferably 0 to 4° C., in particular 2 to 19° C., in particular 3 to 18° C., and preferably 4 to 15° C. before they are tempered, i.e., heated.

In another preferred embodiment, a method of the present invention is provided in which the intracutaneous injection according to method step c) is performed using a syringe having a needle with a diameter of 0.3 to 0.4 mm, in particular 0.32 to 0.38 mm, and preferably 0.35 mm.

In another preferred embodiment, a method of the present invention is provided in which the supplying according to method step a), the mixing according to method step b), and the intracutaneous injection according to method step c) are carried out in a syringe, particularly an at least two-chambered syringe, having a mixing device and a needle with a diameter of 0.3 to 0.4 mm, preferably 0.3 mm, in particular 0.32 to 0.38 mm, and preferably 0.35 mm.

In another preferred embodiment, a method of the present invention is provided in which the mixing is completed in a period of at most 5 seconds.

In another preferred embodiment, a method of the present invention is provided in which the gelling of the prepared collagen composition starts within 10 seconds after the mixing.

In another preferred embodiment, a method of the present invention is provided in which the intracutaneous injection and shaping of the collagen composition lasts at most 4 minutes, preferably at most 2 minutes.

In another preferred embodiment, a method of the present invention is provided in which the mixing of the collagen solution and the buffer solution is achieved by expulsion of the solutions from the chambers of the syringe and merging of the solution streams in a mixing device allocated to the syringe, wherein the prepared collagen composition exits the mixing device.

In another preferred embodiment, a method, a syringe, or a kit of the present invention is provided in which the liquid gellable collagen composition prepared from the collagen solution employed has a concentration of 6 to 12 mg/mL, in particular 7 to 11 mg/mL, preferably 6 to 10 mg/mL, in particular 9 to 11 mg/mL, in particular 7 to 9 mg/mL, preferably 8 to 10 mg/mL, and in particular 8 mg/mL.

In a particularly preferred embodiment, provision is made such that the collagen solution employed, which after mixing with a neutralizing buffer solution leads to the supplying of the liquid gellable collagen composition, has a collagen concentration of 8 to 16 mg/mL, preferably 9 to 16 mg/mL, in particular 8 to 12 mg/mL, in particular 10 to 15 mg/mL, preferably 9 to 13 mg/mL, with preference given to 9 to 11 mg/mL, in particular 10 mg/mL.

In another preferred embodiment, a method or a kit of the present invention is provided, wherein the pH of the collagen solution (based on a temperature of 21° C.) is 6 or lower.

In another preferred embodiment, a method, a syringe, or a kit of the present invention is provided, wherein the collagen solution, in particular the collagen solution supplied in method step a), was produced by acid extraction without using enzymatic activity from collagen-containing tissue, in particular rat tails.

Such a collagen solution produced from collagen-containing tissue by acid extraction without using enzymatic activity is preferably rendered gellable by mixing it with a neutralizing agent, e.g., a neutralizing buffer solution, which initiates the gelling process owing to the resultant increase in the pH.

In a particularly preferred embodiment, the collagen of the collagen solution is native collagen.

In another preferred embodiment, a method, a syringe, or a kit of the present invention is provided, wherein the collagen solution, the liquid gellable collagen composition, or both are cell-free.

In a particularly preferred embodiment, the method has at least the following steps: Separately supplied collagen solution and buffer solution, which in particular were cold stored beforehand, are each brought to a temperature of 20° C. to about 37° C., preferably to about 30° C.; the tempered collagen solution and the tempered buffer solution are then mixed, preferably immediately thereafter, wherein a liquid gellable collagen composition is obtained, which starts to gel immediately after injection into the patient's dermis and is able to cure into a collagen biomatrix.

Particular preference is given to provision being made such that the collagen solution and the buffer solution are not mixed until the application, i.e., in particular during the application of the collagen composition, and only form the initially still-liquid gelling collagen composition during the application. According to the invention, preference is thus given to applying the gelling but still-liquid collagen composition in the nascent state, which can then cure at the application site, specifically the dermis.

According to the invention, preference is given to supplying a concentrated collagen solution with a collagen concentration of preferably 8 to 16 mg/mL, preferably 9 to 16 mg/mL, in particular 10 to 15 mg/mL, preferably 8 to 12 mg/mL, in particular 10 mg/mL and a buffer solution, which can be stored together unmixed but in an integral container and under refrigeration in a manner known per se, particularly at temperatures of about 0° C. to about 4° C. In the scope of the method of the invention, shortly before these solutions are used for producing the collagen biomatrix in situ, they are brought to, for example, room temperature (i.e., in particular 20° C. or higher) or to body temperature (i.e., in particular about 30° C., especially 20 to 37° C.).

Particular preference is given to tempering the collagen solution and the buffer solution simultaneously, especially immediately prior to the mixing and dispensing according to the invention. This can be accomplished by brief storage in a heating cabinet or optionally by hand warming. According to the invention, particular preference is given to making provision for avoiding a collagen solution temperature greater than 37° C.

According to the invention, particular preference is given to not mixing the tempered solutions until immediately before application to the intracutaneous target site for forming the gellable collagen composition, which starts to gel immediately during the application and, preferably after having been molded, finishes gelling (i.e., cures) in the application site.

Both the collagen solution and the buffer solution are in liquid form prior to use or application. Preference is given to the collagen solution and/or the buffer solution being aqueous solutions. The viscosity thereof advantageously allows the immediate mixing thereof without additional denaturing measures such as heating. The dynamic viscosity of the buffer solution is preferably in the range of that of water or slightly mobile aqueous solutions, i.e., about 1 to 5 mPa·s.

Preference is given to supplying the collagen solution and the buffer solution separately from one another initially, preferably in a multi-chamber syringe; particular preference is given to them being tempered separately from each other in the syringe and mixed immediately upon discharge from the syringe. In another embodiment of the invention, provision can also be made for mixing the collagen solution and the buffer solution with each other and then tempering the gellable collagen composition in this mixed form. Particular preference is given to making provision such that the combining and mixing of the collagen solution and the buffer solution are achieved by expulsion of the solutions from the chambers of the syringe and by merging of the solution streams in the interior of the syringe in a mixing device allocated to the syringe, wherein the freshly prepared collagen composition exits via the outlet of the mixing device.

The invention preferably makes provision such that the preferably concentrated collagen solution provided in connection with the method, kit, or syringe of the invention is extracted from collagen-containing tissue directly and without denaturing steps. In a preferred embodiment, the collagen-containing solution is obtained from the collagen-containing tissue without using enzymes. In a particularly preferred embodiment, the collagen-containing solution is obtained from the collagen-containing tissue without using bases. In a particularly preferred embodiment, the collagen-containing solution is obtained from the collagen-containing tissue without using enzymes and bases. In a particularly preferred embodiment, the collagen-containing solution is obtained from the collagen-containing tissue without using steps that would mechanically damage the collagen to be obtained, for instance without using homogenizations. Prepared rat tail tendons are a preferred collagen-containing tissue. The collagen is preferably obtained therefrom by means of acid, particularly acetic acid extraction, and in particular the collagen is obtained by means of acid extraction alone, that is without any other method steps.

In a particularly preferred embodiment, a collagen solution for use according to the invention is obtained from rat tails, wherein collagen fibers are dissolved out of rat tails from which the skin has been removed, incubated in acetic acid solution, in particular with refrigeration, wherein undissolved collagen fractions are centrifuged and filtered from dissolved collagen fractions, and wherein the dissolved collagen fractions precipitate out and are rinsed with buffer solution, frozen, and freeze-dried. The freeze-dried collagen preparation thus obtained is then reconstituted in acetic acid so that a collagen content of 8 to 16 mg/mL, preferably 9 to 16 mg/mL, in particular 10 to 15 mg/mL, preferably 8 to 12 mg/mL, and in particular 10 mg/mL is obtained.

In a particularly preferred embodiment, the collagen solution for use according to the invention is produced as in Example 1, step i).

In a particularly preferred embodiment, the obtained collagen-containing solution, i.e., the collagen solution, is in principle, in other words potentially capable of gelling, meaning that it can cure. In a preferred embodiment, the collagen-containing solution is obtained from the collagen-containing tissue by means of acid extraction, wherein in this embodiment its actual gellability is conferred by adding a pH-increasing agent, in particular a buffer solution with neutralizing properties.

In a preferred embodiment, an acidic collagen solution as a collagen solution is provided, particularly one which has a collagen content (collagen concentration) greater than 8 mg/mL, in particular about 9 mg/mL, and greater than or preferably up to about 16 mg/mL. In a particularly preferred embodiment, the collagen concentration of the preferably concentrated collagen solution, in particular of the acidic collagen solution, is in the range of 8 to 16 mg/mL, preferably 9 to 16 mg/mL, in particular 10 to 15 mg/mL, in particular 8 to 12 mg/mL, in particular 9 to 11 mg/mL, and preferably 10 mg/mL. Preference is given to the preferably concentrated collagen solution being acidic, in particular in order to maintain its viscosity. The pH of this collagen solution (based on a temperature of 21° C.) is thus 6 or lower, in particular 5 to 3.5.

In a special embodiment, this collagen solution does not contain any other additives or auxiliary materials such as cells, cell components, growth factors such as cytokines, immune stimulants, antibiotics, or stabilizers such as polysaccharides. In an alternative embodiment, at least one such additive or auxiliary material is contained in the collagen solution.

In another embodiment of the invention, this collagen solution does not contain any particulate materials, in particular no microcarriers, beads, or the like.

In order to obtain the gelling collagen composition, this preferably acidic collagen solution is mixed with a neutralizing agent, in particular a buffer. In the simplest case, the neutralizing buffer is a buffer salt solution known per se, by means of which the pH value of the collagen composition is brought into a neutral range, in particular a pH of 7.0 to 7.5 (based on a temperature of 21° C.). Preference is given to using a HEPES buffered saline with a pH of 8.3, which can be prepared in a manner known per se. According to the invention, the buffer solution furthermore serves to dilute this collagen solution in order to reach the desired final concentration in the gelling collagen composition. Depending upon the intended ratio of the mixture with this collagen solution, the buffer composition is preferably at least 2× concentrated (1+1), at most 10× concentrated (9+1), and preferably 5× concentrated (4+1).

In a special embodiment, the buffer solution or the collagen solution does not contain any other additives or auxiliary materials such as cells, cell components, growth factors such as cytokines, immune stimulants, or stabilizers such as polysaccharides. In an alternative embodiment, cells and optionally at least one other additive or auxiliary material are contained in the buffer solution or the collagen solution, which during the mixing with the concentrated collagen solution according to the invention form a cell-containing gelling collagen composition, which cures into a cell-containing collagen transplant. In a special alternative thereof, the cells are fibroblasts, notably autologous cells or stem cells.

In a particularly preferred embodiment of the present invention, the buffer solution also does not contain any particulate materials such as beads and/or microcarriers or the like.

Preference is given to providing for the collagen solution and the buffer solution to be mixed in a volume ratio of 1:1 to 9:1 (collagen solution to buffer solution). Preference is given to mixture ratios of 4:1, in other words four parts collagen solution to one part buffer solution.

The collagen content in the prepared liquid, in particular aqueous gellable collagen composition is preferably at least 6 mg/mL or greater, especially 6 to 12 mg/mL, in particular 6 to 10 mg/mL. In a preferred alternative thereof, the content of collagen in the gellable collagen composition is about 8 mg/mL.

Preference is given to using a multi-chambered syringe. Particular preference is given to the latter being a single-use syringe known per se. In a preferred alternative, the syringe is equipped with a mixing device in the form of a static mixer known per se. In addition other integral mixing devices, which allow a mixing of separate solutions during application, are known to persons skilled in the art. Such other arrangements in alternative embodiments are likewise the subject matter of the invention.

If the collagen solution and the buffer solution are supplied in a multi-chambered syringe, particular preference is given to the latter having chamber volumes of about 0.1 to about 10 mL in each case. The tempering of the solutions preferred according to the invention preferably takes place in the interior of the syringe, and the mixing of the collagen solution and the buffer solution preferably takes place as the solution is discharged from the syringe. Preference is given to making provision such that the mixing device of the syringe is a static mixer known per se. A person skilled in the art is familiar with alternative mixing devices that can be used in connection with syringes. Depending upon syringe volume and discharge speed, the discharge process should take about 1 to 60 seconds. According to the invention, the mixing time for each infinitesimal volume fraction exiting both chambers is preferably about 0.5 to about 2 seconds.

The nascent composition begins to gel immediately, particularly preferably within 10 seconds after mixing, preferably within 5 seconds. The gelling composition is still liquid and above all still flowable. The gelling process is complete when the collagen composition cures into a solid biomatrix. The curing into a biomatrix is preferably complete within 2 to 4 minutes. The curing of the initially still-flowable collagen composition therefore preferably does not take place until the latter has been injected in the dermis so that if desired, a shaping, in other words three-dimensional molding, is possible before the gelling process is complete.

In this connection the invention also provides a pre-filled syringe, particularly in the form of a single-use syringe, wherein the syringe comprises at least two separate chambers which open into a syringe mechanism allocated to the syringe via which the contents of each chamber can preferably be administered simultaneously, and wherein the syringe has a needle with an outer diameter of 0.3 to 0.4 mm, preferably 0.3 mm, preferably 0.32 to 0.38 mm, and in particular 0.35 mm. According to the invention, the syringe is at least further characterized in that at least a first chamber is filled with the liquid concentrated collagen solution and at least a second chamber separate therefrom is filled with the buffer solution. In addition the syringe can be provided with other such chambers, which can be filled with additives or auxiliary materials.

Together with a package insert indicating intracutaneous application to treat skin defects associated with, e.g., skin diseases or signs of skin aging, the syringe filled with at least the collagen solution and the buffer solution of the invention constitutes a kit that can be used to produce a collagen composition that gels immediately.

In a preferred embodiment, such a kit can comprise a container containing a collagen solution and a container containing a neutralizing buffer solution.

Moreover, the invention is not limited to the use of a filled multi-chambered syringe. Embodiments which allow a separate storage of concentrated collagen solution and buffer solution and the subsequent direct mixing of these solutions for preparing the gelling collagen composition are also provided. An alternative embodiment is in particular a multi-chambered, single-use mixing capsule, which can be used in conjunction with a capsule mixer known per se.

The use of the filled syringe of the invention or of the kit of the invention to administer the medical therapy are likewise the subject matter of the invention. A special application is the prophylactic or therapeutic treatment of skin defects, in particular skin diseases and signs of skin aging of the human or animal body, by intracutaneous filling of the collagen structure in the connective tissue of the skin of the body.

In connection with the present invention, skin defects are understood to mean skin diseases and signs of skin aging in particular. Skin defects in the sense of the present invention can also be symptoms arising as part of or in the context of skin diseases and signs of skin aging, or symptoms associated with these conditions.

In connection with the present invention, skin defects are understood to mean all skin phenomena deviating from the normal condition of the skin of a healthy human or animal body, which can be treated prophylactically (i.e., prevented) or therapeutically, in particular repaired, by intracutaneous filling of the collagen structure of the skin. The underlying causes of such skin defects, e.g., skin diseases or signs of skin aging, may be injuries, aging processes, and the impact of external influences such as radiation, heat, fire, liquids or the like. Such skin defects are also understood to include skin defects of a cosmetic nature, in other words ones of a more esthetic rather than a medical nature. Skin defects of a cosmetic nature can also be skin phenomena identified by the patient or his/her milieu as improvable, in particular embellishable, but not requiring therapy for medical reasons. The present invention relates in particular to skin defects in the form of wrinkles.

The invention will be described in more detail with reference to the figures and the following exemplary embodiments, which are not to be understood as limiting.

FIG. 1 shows a schematic illustration of an embodiment of the filled syringe of the invention as a means for carrying out the method of the invention.

In the embodiment illustrated, two separate, parallel, cylindrical chambers (11, 12) for holding the collagen solution on the one hand and the buffer solution on the other are configured in an integral container. Both chambers open at the front into a common outlet channel (18) of a static mixer (16), wherein there is a mixing baffle in the mixer. Upstream of the outlet channel (18) is a needle with an outer diameter of 0.3 mm. Coupled syringe plungers (14) are provided for emptying the chambers (11, 12) in order to apply and prepare the collagen composition. Said plungers form the rear boundary of the volume of the chambers: in a manner known per se the contents can be expelled from both chambers (11, 12) simultaneously by applying pressure to the plungers (14). Depending on the ratio of the structurally determined volume of the chambers (11, 12), upon expulsion a uniform mixing of the liquid contained in the chambers (11, 12) takes place in this volume ratio. In the embodiment illustrated, the volume ratio of the chambers (11, 12) is 1:1.

Figure 1:
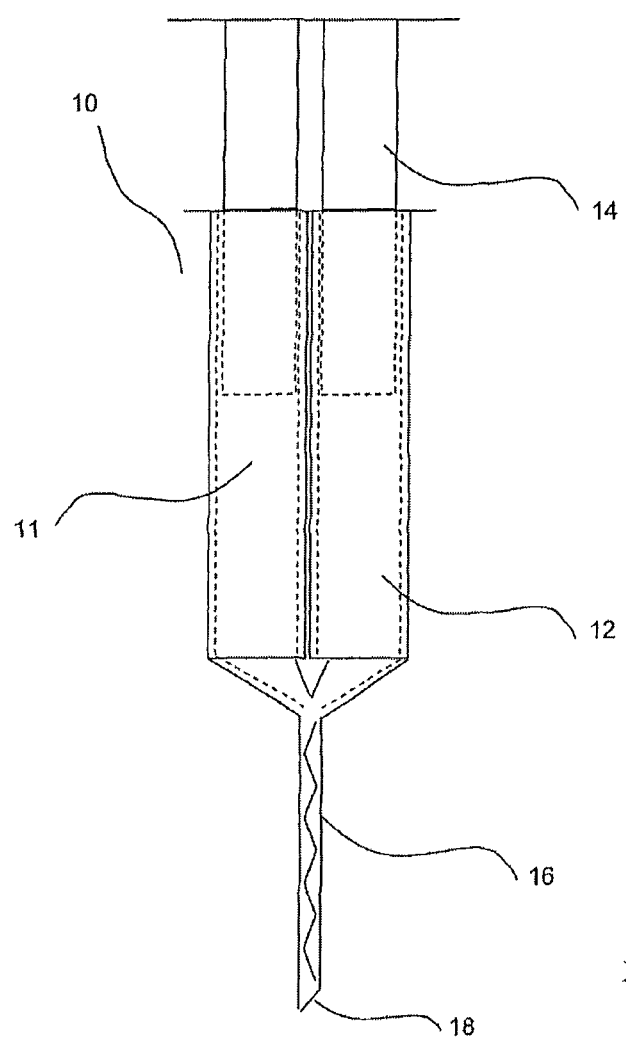

EXAMPLE 1: PREPARATION OF AN IMMEDIATELY GELLING LIQUID COLLAGEN COMPOSITION i) To prepare a concentrated collagen solution, rat tails are stored at about minus 20° C. and then surface-disinfected for a few minutes in about 70% alcohol. The skin is pulled off and the individual collagen fibers are dissolved out. The collagen fibers are surface-disinfected in alcohol again, washed with PBS afterwards, and then transferred to a about 0.1% (0.5 mol/L) acetic acid solution and incubated therein. The collagen fibers are kept in the acetic acid solution, with stirring and under refrigeration (ca. 0 to 4° C.), for a period of at least 7 days. After separation of the undissolved collagen fractions at the end of the incubation period, the collagen is filtered and precipitated out. The precipitate is rinsed with buffer solution, frozen, and then freeze-dried. The freeze-dried collagen is reconstituted in 0.1% acetic acid in a defined manner such that a collagen content of 8 to 16 mg/mL, in particular 9 to 16 mg/mL is obtained. The pH of the concentrated collagen solution is about 4.0.

ii) For mixing four parts of collagen solution with one part of neutralizing buffer solution (4+1), a 5× concentrated buffer solution is prepared. In particular a solution of 35.6 g NaCl in 937.5 mL of ultra-pure water with 62.5 mL 3 mol/L HEPES solution is prepared as a 5× concentrated buffer solution. The pH of the buffer solution is adjusted with NaOH to 8.3 prior to use.

Collagen solution and buffer solution are filled into separate chambers of a multi-chambered syringe with a chamber volume ratio of 1:4, respectively, and cold stored at about −15° C. or colder until further use.

iii) To produce a collagen-containing biomatrix, the multi-chambered syringe is briefly placed in a heating cabinet or a water bath, thus heating the collagen solution and the buffer solution to a temperature of about 30° C. For mixing the two solutions, the latter are expelled from the multi-chambered syringe by the coupled syringe plungers. Both solutions are conveyed through the mixing device connected to the chambers. The mixed, immediately gelling collagen composition exits the syringe. The composition is filled into a mold while still in liquid form. Once dispensed, the collagen composition completely fills the mold and within a few minutes it cures into a solid, collagen-containing biomatrix. At a collagen content of about 8 mg/mL of the liquid collagen composition resulting from the mixing with buffer solution and a temperature of about 30° C., curing is complete within 2 minutes.

EXAMPLE 2: GELLING OF A COLLAGEN COMPOSITION

The collagen compositions prepared according to Example 1 undergo rheological tests to determine the elastic modulus. Collagen solution (10 mg/mL) and buffer solution as in Example 1 are filled into two-chambered syringes (e.g., Medmix Systems, Switzerland) (collagen chamber: 4 parts collagen solution, 2 mL; buffer chamber: 1 part 5X concentrated buffer, 0.5 mL) and frozen.

An hour of gentle thawing at room temperature (20.5° C.) is followed by ten minutes of tempering of the syringes in a water bath at various temperatures ranging from 20 to 40° C. (Table 1).

TABLE 1

| Target temperature [° C.] (Actual temperature range [° C.]) | No. syringes tested |
|---|---|
| 20 (19-20) | 3 |
| 30 (30-31) | 4 |
| 37 (36.5-37) | 4 |
| 38 (38-39) | 3 |
| 40 (40-41) | 4 |

For mixing the two components after tempering, the stopper of the syringe is replaced with a mixing adapter and the contents are carefully deposited in a well of a 12-well tissue culture plate, discarding the first two drops dispensed.

The complete gelling of the collagen composition (8 mg/mL collagen), in other words curing into a solid gel, took place in 15 min. at 20.5° C. A visual consistency rating is then performed (Table 2).

Figure 2:
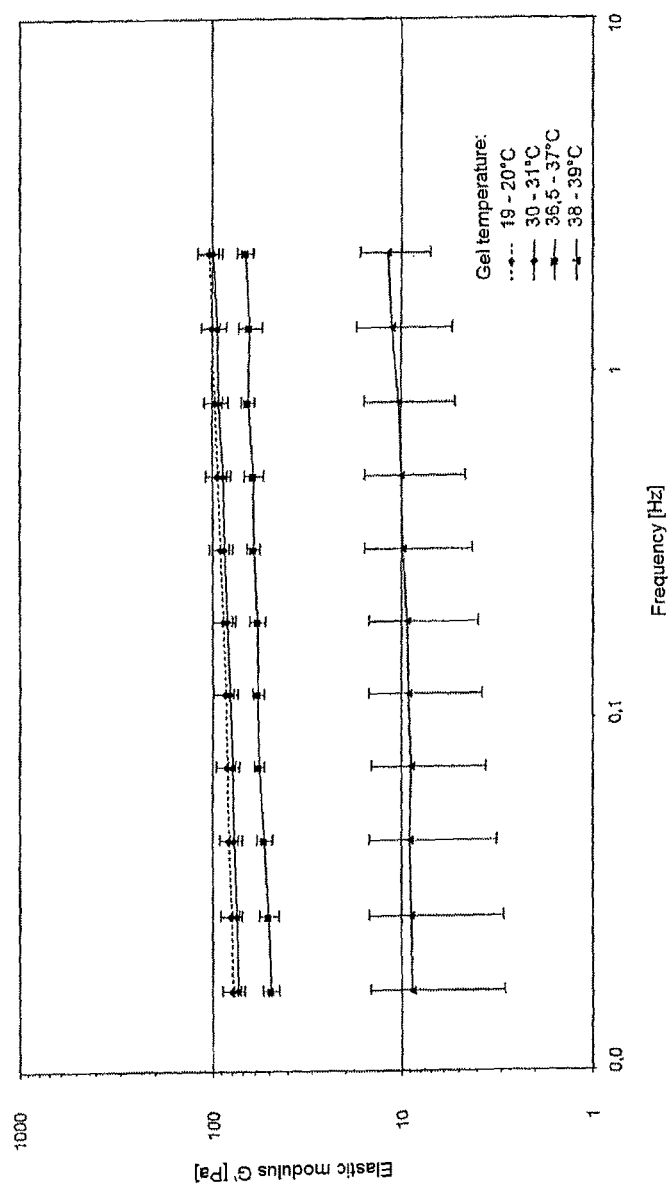
FIG. 2 shows the results of rheological tests on collagen gels: elastic modulus as a function of test frequency (means and standard deviations) for differently pre-tempered two-chambered syringes.

The elastic moduli of the gels outside the well are then determined by the frequency method (Bohlin CVO R 150, Malvern Instruments GmbH, Germany) (FIG. 2).

TABLE 2

| Target temperature [° C.] (Actual temperature range [° C.]) | Consistency of the gels after 15 min |
|---|---|
| 20 (19-20) | solid |
| 30 (30-31) | solid |
| 37 (36.5-37) | solid |
| 38 (38-39) | semi-solid |
| 40 (40-41) | liquid |

From FIG. 2 it can be discerned that the highest calculated means of the elastic modulus lie within a temperature range of between 20 and 30° C. Although the curve of the collagen heated to 37° C. runs somewhat lower, these gels also showed a firm consistency upon visual inspection. When heated to 38° C., the gels were only semi-solid and had very low values with large fluctuations in the oscillatory tests. At 40° C. the collagen no longer gels.

EXAMPLE 3: RHEOLOGICAL MEASUREMENTS TO DETERMINE VISCOSITY

Apparatus:
  C-VOR 150 CE/WIN Rheometer System with air filter unit, Bohlin Pforzheim
  Peltier System 180° for CVO for temperatures of −30° C. to 180° C.
  Water-cooling unit
  CP 4°/40-mm cone-plate measuring system
  Computer: see 06SOP-01-010
Software: Viscometry software module
Measurement of the Viscosity of Collagen The measurements are taken at a shear rate of 0.32 to 56.23 s−1. The viscosity of the collagen is measured. Reproducibility is measured after cleaning and refilling the plates.

In the first step, 1,000,000 kg/m$^3$ is input in the rheometer as the density of the material (approximate density of the collagen at 23° C.). The sample (min. 2 mL of collagen) is then deposited in the center of the lower plate and the measuring geometry is lowered (automatic stopping at a preset gap clearance of 150 μm).

Figure 4:
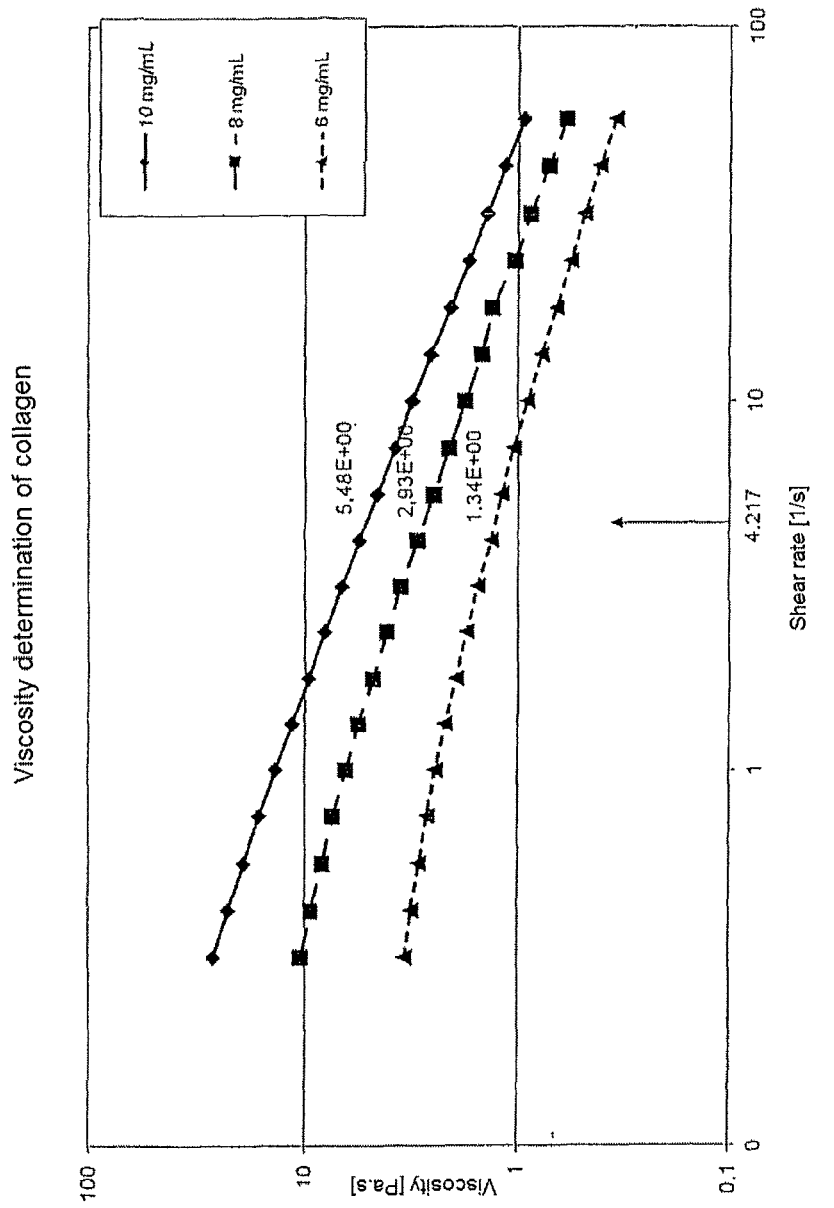
FIG. 4 shows the results of rheological tests to determine the viscosity of liquid collagen compositions for use according to the invention.

Viscosity is measured with the following parameters:
Pre-shearing: 100 s−1
Application time: 10 s
Compensation time: 30 s
Viscometry mode: Shear rate table 0.1 to 100 s−1 (25 values, logarithmic scale)
Delay time: 5 s constant
Integration time: 5 s For the preliminary measurement and the reproducibility measurement, the raw data of the shear rate measurement (0.32 to 56.23 s−1) are compiled in an Excel table and graphed. The results for collagen concentrations of 6, 8, and 10 mg/mL collagen are presented in FIG. 4, wherein the collagen solutions were prepared as in Example 1.

For a shear rate of 4.217/s, viscosities of 1.34 Pa·s, 2.93 Pa·s, and 5.48 Pa·s are obtained for the 6 mg/mL, 8 mg/mL, and 10 mg/mL collagen solutions, respectively.

EXAMPLE 4: APPLICATION IN PIG SKIN

Figure 3:
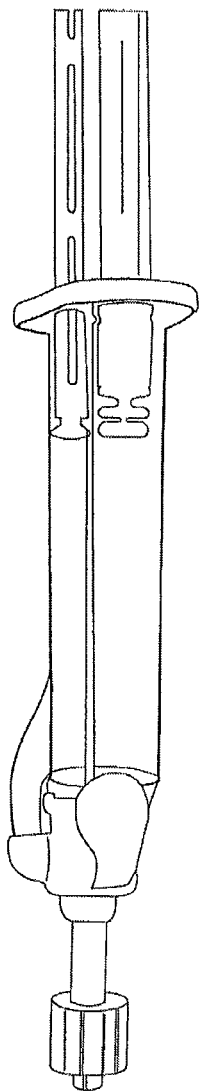
FIG. 3 shows a photographic illustration of the two-chambered syringe illustrated schematically in FIG. 1 and used in Example 4.
Figure 5:
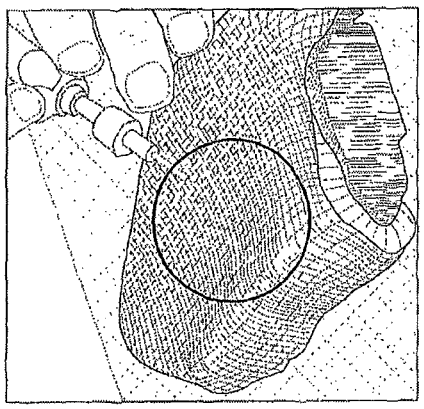
FIGS. 5 to 10 show, in photographic format, the sequence of treatment of a skin defect on a pig skin model made possible according to the invention, with intracutaneous application and subsequent molding of the injected gellable collagen prior to curing.
Figure 6:
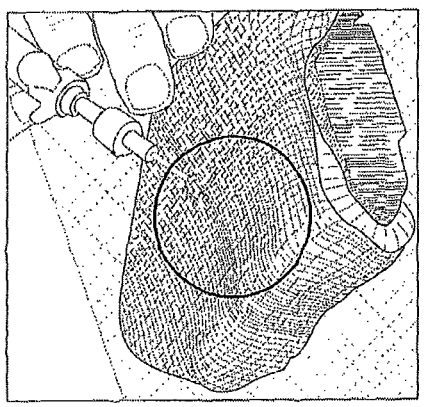
Figure 7:
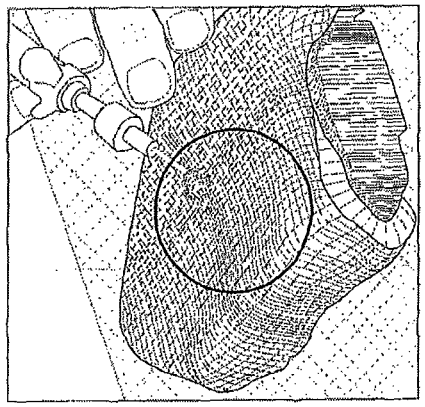
Figure 8:
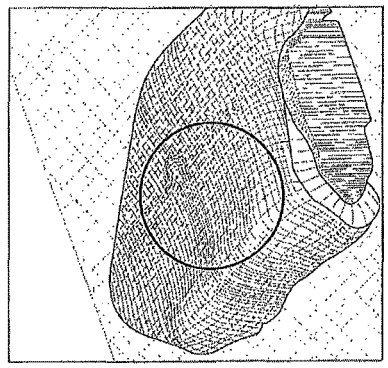
Figure 9:
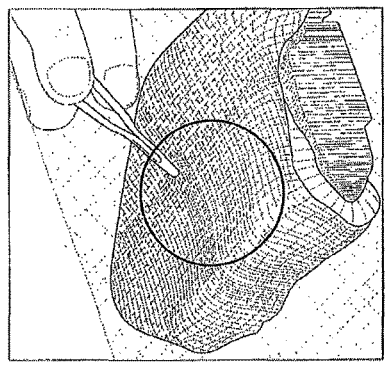
Figure 10:
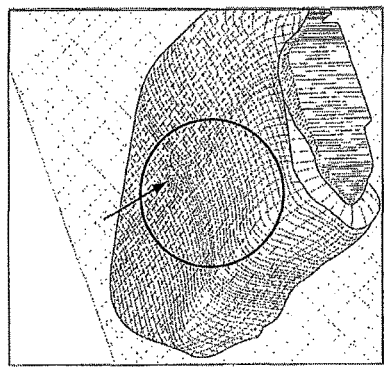

The injectability of the liquid gellable collagen composition supplied through a 30-gauge needle according to the invention was tested in pig skin, using the liquid gellable collagen-buffer mixture according to Example 1 with a native collagen concentration of 8 mg/mL. The samples of 8 mg/mL native collagen-buffer mixture were injected intracutaneously into pig skin (FIGS. 5 to 7) with a two-chambered syringe (FIGS. 1 and 3; chamber 11 filled with 2 mL of a 10 mg/mL collagen solution, chamber 12 filled with 0.5 mL of a buffer solution). The intracutaneously applied, still-liquid collagen-buffer solution (FIG. 8) was then molded from outside (FIG. 9). The outcome of the molded gel is illustrated in FIG. 10. The collagen-buffer solution could be injected intracutaneously with the 30-gauge needle, where it gelled and retained its shape after molding.

The invention claimed is:

1. A method for intracutaneous filling of a collagen structure in connective tissue of a patient's skin with a collagen gel, the method comprising the steps:
   a) separately supplying a collagen solution and a neutralizing buffer solution, and separately tempering the collagen solution and the neutralizing buffer solution by bringing the collagen solution and the neutralizing buffer solution each to a temperature of 20° C. to 37° C., wherein the collagen solution comprises native collagen at a concentration of from 9 mg/ml to 16 mg/ml;
   b) mixing the tempered collagen solution and the tempered neutralizing buffer solution by merging a stream of the tempered collagen solution and a stream of the tempered neutralizing buffer solution together in a mixing device coupled to a syringe to obtain a liquid gellable collagen composition having a native collagen concentration of from 6 mg/ml to 12 mg/ml and a viscosity of 2 to 9 Pa·s;
   c) intracutaneously injecting the liquid gellable collagen composition through a needle coupled to the mixing device and into an intracutaneous target site before gelling of the liquid gellable collagen composition, the needle having an outer diameter of 0.3 to 0.4 mm; and
   d) shaping the injected liquid gellable collagen composition at the intracutaneous target site, wherein the shaped collagen gel cures at the target site.

2. The method according to claim 1, wherein the mixing includes mixing for a maximum period of 5 seconds.

3. The method according to claim 1, further comprising gelling of the prepared collagen composition starting within 10 seconds after the mixing.

4. The method according to claim 1, wherein the intracutaneous injection and the shaping of the collagen composition collectively last at most 4 minutes.

5. The method according to claim 1, wherein the intracutaneous injection and the shaping of the collagen composition collectively last at most 2 minutes.

6. The method according to claim 1, wherein the mixing of the collagen solution and the neutralizing buffer solution is achieved by expulsion of the solutions from chambers of the syringe and merging of solution streams in a mixing device allocated to the syringe, wherein the prepared collagen composition exits the mixing device.

7. The method according to claim 1, wherein the pH of the collagen solution at a temperature of 21° C. is 6 or lower.

8. The method according to claim 1, wherein the collagen solution is produced from collagen-containing tissue by acid extraction without treating with enzyme.

9. The method according to claim 1, wherein at least one of the collagen solution and the liquid gellable collagen composition is cell-free.

10. The method according to claim 1, wherein step a) includes providing at least a first container including the collagen solution and supplying at least a second container including the neutralizing buffer solution.

11. The method according to claim 1, wherein step c) includes instantaneous injection with a syringe having at least two separate containers configured as chambers, the at least two separate containers in fluid connection with a mixing device arranged in the syringe and with the needle of the syringe, wherein at least a first chamber is filled with the collagen solution and at least a second chamber separate therefrom is filled with the neutralizing buffer solution.

12. The method according to claim 1, wherein the shaping of the injected liquid gellable collagen composition at the intracutaneous target site includes molding the injected liquid gellable collagen composition at the intracutaneous target site into a three-dimensional structure with a desired shape before the liquid gellable collagen composition completely cures.

13. The method according to claim 1, wherein the neutralizing buffer solution is a buffer salt solution having a pH of 8.3.

14. The method according to claim 13, wherein the buffer salt solution is HEPES buffered saline.

15. The method according to claim 1, wherein the mixing of the collagen solution and the neutralizing buffer solution comprising mixing the collagen solution and the neutralizing buffer solution at a collagen solution:buffer solution ratio of 1:1 to 9:1, such that the liquid gellable collagen composition obtained from the mixing has a pH of 7.0 to 7.5.

16. A method for intracutaneous filling of the collagen structure in connective tissue of a patient's skin with a collagen gel, the method comprising:
   a) disposing a collagen solution comprising 9 to 16 mg/mL native collagen and having a pH of 6 or lower, and a neutralizing buffer solution comprising a buffer, a salt, and having a pH of 8.3 in separate chambers of a syringe comprising a needle having an outlet channel in fluid communication with the separate chambers by way of a mixing device, and coupled syringe plungers for emptying the separate chambers;
   b) tempering the syringe such that the collagen solution and the neutralizing buffer solution are heated to a temperature of from 20° C. to 37° C. to obtain a tempered collagen solution and a tempered neutralizing buffer solution;
   c) piercing the patient's skin with the needle and positioning the outlet channel at a target site;
   d) depressing the coupled syringe plungers, wherein the depressing causes:
      mixing of the tempered collagen solution with the tempered neutralizing buffer solution in the mixing device by expelling the tempered collagen solution and the tempered neutralizing buffer solution from their respective chambers and merging the tempered collagen solution and the tempered neutralizing buffer solution into the mixing device to obtain a liquid gellable collagen composition comprising 6 to 12 mg/mL native collagen, a pH of 7.0 to 7.5, and a viscosity of 2 to 9 Pa·s, and
      injecting the liquid gellable collagen composition intracutaneously at the target site of the patient's skin through the outlet channel of the needle, wherein the needle has an outer diameter of 0.3 to 0.4 mm; and
   e) molding the liquid gellable collagen composition within the patient's skin into a three-dimensional structure with a desired shape,
   wherein the liquid gellable collagen composition cures in situ within the patient's skin and retains the desired shape.

17. The method according to claim 16, wherein the needle has an outer diameter of 0.32 to 0.38 mm.

18. The method according to claim 16, wherein:
   the neutralizing buffer solution is 5× concentrated,
   the syringe comprises two separate chambers with a chamber volume ratio of 1:4 for receiving the 5× neutralizing buffer solution and the collagen solution, respectively,
   the tempering comprises bringing the collagen solution and the neutralizing buffer solution each to a temperature of about 30° C., and
   the liquid gellable collagen composition has a collagen content of about 8 mg/m L.

* * * * *